(12) United States Patent
Okawa et al.

(10) Patent No.: US 7,138,567 B2
(45) Date of Patent: Nov. 21, 2006

(54) GA20 OXIDASE FROM RICE AND USES THEREOF

(75) Inventors: Miho Okawa, Tsukuba (JP); Makoto Matsuoka, Nagoya (JP); Motoyuki Ashikari, Nagoya (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 10/481,381

(22) PCT Filed: Jun. 7, 2002

(86) PCT No.: PCT/JP02/05678

§ 371 (c)(1), (2), (4) Date: Jun. 28, 2004

(87) PCT Pub. No.: WO03/006655

PCT Pub. Date: Jan. 23, 2003

(65) Prior Publication Data

US 2004/0250315 A1 Dec. 9, 2004

(30) Foreign Application Priority Data

Jun. 19, 2001 (JP) .............................. 2001-185128

(51) Int. Cl.
- *C12N 15/82* (2006.01)
- *A01H 5/00* (2006.01)
- *C07H 21/04* (2006.01)

(52) U.S. Cl. .................. 800/290; 800/278; 800/320.2; 435/468; 435/419; 435/320.1; 536/23.6; 536/23.2

(58) Field of Classification Search ................ 800/290, 800/278; 536/23.2, 23.6, 24.5, 23.1; 435/320.1
See application file for complete search history.

(56) References Cited

U.S. PATENT DOCUMENTS 5,702,933 A * 12/1997 Klee et al. .................. 800/283

FOREIGN PATENT DOCUMENTS

| JP | 11-290082 | 10/1999 |
|---|---|---|
| JP | 2000-4884 | 1/2000 |
| WO | WO 03/070934 A1 | 8/2003 |

OTHER PUBLICATIONS

Kim Y, Buckley K, Costa MA, and An G. Plant Molecular Biology (1994) vol. 24, pp. 105-117.*
Colliver SP, Morris P, and Robbins MP. Plant Molecular Biology (1997) vol. 35, pp. 509-522.*
Elomaa P, Helariutta Y, Kotilainen M, and Teeri TH. Molecular Breeding (1996) vol. 2, pp. 41-50.*
Coles JP, Phillips AL, Croker SJ, Carcia-Lepe R, Lewis MJ, and Hedden P. The Plant Journal (1999) vol. 17, pp. 547-556.*
Yoon U-H, Hahn J-H, and Eun M-Y GenBank Accession # AF254556 (2001).*
Sasaki A, Ashikari M, Ueguchi-Tanaka M, Itoh H, Nishimura A, Swapan D, Ishiyama K, Saito T, Kobayashi M, Khush GS, Kitano H, and Matsuoka M. Nature (2002) vol. 416, pp. 701-702.*
Matsuoka M, Sasaki A, Ashikari M. GenBank Accession # AB077025 (2002).*
GenBank Acc. No. AF465255 for *Oryza sativa* cultivar Nipponbare gibberellin-20 oxidase (Sd-1) gene, complete cds.
Hedden et al. "Gibberellin biosynthesis: Enzymes, genes and their regulation." *Ann. Rev. Plant Physio. Plant Mol. Biol.* 1997;48:431-60.
Kusaba et al. "Decreased GA1 content caused by the overexpression of OSH1 is accompanied by suppression of GA 20-oxidase gene expression." *Plant Physiol.* Aug. 1998;117(4):1179-84.
Lange et al. "Expression cloning of a gibberellin 20-oxidase, a multifunctional enzyme involved in gibberellin biosynthesis." *PNAS USA* Aug. 30, 1994;91(18):8552-6.
Maeda et al. "High density molecular map of semidwarfing gene, sd-1, in rice (*Oryza sativa* L.)." *Breeding Science* 1997;47:317-20.
Phillips et al. "Isolation and expression of three gibberellin 20-oxidase cDNA clones from *Arabidopsis.*" *Plant Physiol.* Jul. 1995;108(3):1049-57.
Sasaki et al. "A mutant gibberellin-synthesis gene in rice." *Nature* 2002;416:701-2.
Toyomasu et al. "Cloning and characterization of a cDNA encoding gibberellin 20-oxidase from rice (*Oryza sativa*) seedlings." *Physiologica Plantarum* 1997;99:111-8.
Xu et al. "The GA5 locus of *Arabidopsis thaliana* encodes a multifunctional gibberellin 20-oxidase: molecular cloning and functional expression." *PNAS USA* Jul. 1995 3;92(14):6640-4.

(Continued)

*Primary Examiner*—Anne Kubelik
*Assistant Examiner*—Cathy Kingdon Worley
(74) *Attorney, Agent, or Firm*—Lahive & Cockfield, LLP; Elizabeth A. Hanley, Esq.; Jeanne M. DiGiorgio, Esq.

(57) ABSTRACT

The present inventors presumed that the sd1 gene was the C20 oxidase gene, and isolated and identified the rice counterpart of *Arbidopsis* C20 oxidase gene. As a result, it was revealed that the rice sd1 gene encodes a novel C20 oxidase. Further studies showed that mutation in this gene led to plant semidwarfing. Utilization of the plant sd1 gene is expected to increase the yield of plants, particularly useful agricultural crops and ornamental plants, to add aesthetic value to ornamental plants through dwarfing, and also to increase the yield and efficient breeding of dwarfed plants by marker selection.

8 Claims, 1 Drawing Sheet

OTHER PUBLICATIONS

EMBL Accession No. AF254556, *Oryza sativa* gibberellin 20 oxidase (GA5) gene, partial sequence. Mar. 14, 2001.

GeneBank Accession No. AF312859. Giardia Intestinalis L-Serine Dehydratase SD1 Gene, Complete CDS. Jun. 18, 2001.

GeneBank Accession No. AY214004. Ceratocytis Resinfera Syctalone Dehydratase 1 (SD1) gene, complete CDS. Mar. 10, 2004.

Keqiang Wu, et al. "Molecular Cloning and Photoperiod-Regulated Expression of Gibberellin 20-Oxidase from the Long-Day Plant Spinach." *Plant Physiol.* (1996) 110:547-554.

Hedden, Peter et al, "Genetic Analysis of Gibberellin Biosynthesis," *Plant Physiology*, vol. 119:365-370 (1999).

Shohab, Youssefian, et al., "The Annual Report of the Plant Biotechnology Institute," pp. 26-27, Mar. 31, 2000.

Spielmeyer, Wolfgang, et al., "Semidwarf (sd-1), 'green revolution' rice, contains a defective gibberellin 20-oxidase gene," *PNAS*, vol. 99:9043-9048 (2002).

\* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
ccgctcgccg agaagcgccg                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2
atgaaggtgt cgccgatgtt                                                      20

<210> SEQ ID NO 3
<211> LENGTH: 5575
<212> TYPE: DNA
<213> ORGANISM: Oryza sativa

<400> SEQUENCE: 3
gtatatttac tagttaacga catcatgtat taaaaatcgg aggaggtata gaagtatgtt          60
ctcctttctt gtaaacatag gttgatctgt atatttgttt ttgtcttatt ttgttttttc        120
attgatctca ccattaaaca ggtggcctcc aaaaatgcat gcagccatgt atcttcccag        180
tccatgaaat taatcttgaa ttattataaa ttaaaaacat attaggattt gatatatgaa        240
aggtataatg gtagcagatc tatcatagaa aacctataac acgtagatga ccgagtagag        300
```

-continued

```
aaaaaagata tacccaacat aatcaagtac cttgttaatt agtaagaagt aagaaamcca    360
tataaataca agcatttggg tgaagctaga atgggaacta tattaccatg tatcccatac    420
atatctatta cgcacttaat acctgaatta ttcgtgtaac aagaacatg ctttggtaaa     480 aaataaaata tttggaccgt ataccatgcg gttatcgcag ttatcacgtg cggtaatatt    540
ctcagttttt caaaccgcgg tataacttgc aataaccgcg tggttttcgc ggtaaccacc    600
aaaccgtggg gctgtggtaa ccccacctaa aacgatttgg taaaccctag tcagagctag    660
cttgatcgtg gctccgccct ctgcatctcc tcatggtcac aagatcaatt tagaacctct    720
tataagctgt tgaaccatca gtactacagt cccaagatta acatatttt taaaatatca     780 aaattgctca tgatgaattg attaccgttc atgtgcctgt atggtgcatg ggtggtatag    840
tgcaccgtga cctgtactgt gctagatgtt ccttccaacc ttagtacttc acgaaaagga    900
gaggaaccat ttccctgtca ccttcctgca acatggtcag gcataaacca aacacgatcg    960
aagcgaatcg gcgataccac acaatagccg cgcgtcgcaa acaacaattc cgcggctagc   1020
tacttccgac ctccgaaact actgcgagcc aagtgggta cggttttagt gcaaataggg    1080
taagtcttgt ttacatcata tcggtttcat tttggtacac gaatggagaa gaaatgaaag   1140
agatcgaaaa aaggaagagc tcgctgtgta tctgtctcgt aacagccccg gtgttacacg   1200
tgctctaaga gagattaatt aaatcgataa gctaccagag gtttagttt ccacgtgtta    1260 attagattgg aaagcgagag aaattaaaaa tagcgagtaa aaatagagat aaccttattg   1320
ctattttgtt ttttttccag caacaaactt atctttcagg ctagtttagg cgatcgctta   1380
gattccgcat cgtcctttc actatttttt ttctgtcagt gacaatgtga aaatttattg    1440
gacagacgac tagcttgtgg tactagctag gaaattccct atcctcgata tgaacaactt   1500
actcaactca gtagagtagc aaatgcccaa gaaagcccga gtcaatctat ttggaaatcc   1560
aatctatttt ctcgtattcg tgtgggaaat caagctatac tagttgaaat tcaccggaag   1620
aaatgcacgg cacttcaata taccaaaatt gcaaggaga atcattcgat taacagtgga    1680
attcaaccaa gaaatgaaaa ggtatatata ggaaatgcac tccaaccacc aaccaataag   1740
tgattccggg caatcaattc tatccgcgag ttgtgggtct gttcagattc attatattag   1800
aacgcgtcac gtaatggatg gagtattata caacaccatt ggttttgcca ctagtgttaa    1860
ctctaataca tgggggttag ttttaccttt aaacttggtc taaaaggatg gacatatggc   1920
aatgcaattg catgggggtc attgattcga ccatcatgtc tgtccagtgg caaccccctc   1980
cctcatcccc tgtggtgggc ccccacggc gctcgtcttc tcccctgtta caaatacccc    2040
accctcctgc ccagacagct cgccctgcac acacacacac actcacactc acacgcctc    2100 tcaactcact cccgctcaac acagcgctca cttctcatct ccaatctcat ggtggccgag   2160
caccccacgc caccacagcc gcaccaacca ccgcccatgg actccaccgc cggctctggc   2220
attgccgccc cggcggcggc ggcggtgtgc gacctgagga tggagcccaa gatcccggag   2280
ccattcgtgt ggccgaacgg cgacgcgagg ccggcgtcgg cggcggagct ggacatgccc   2340
gtggtcgacg tgggcgtgct ccgcgacggc gacgccgagg ggctgcgccg cgccgcggcg   2400
caggtggccg ccgcgtgcgc cacgcacggg ttcttccagg tgtccgagca gggcgtcga    2460 cgccgctctg gcgcgcgccg cgctcgacgg cgccagcgac ttcttccgcc tcccgctcgc   2520
cgagaagcgc cgcgcgcgcc gcgtcccggg caccgtgtcc ggctacacca gcccacgc     2580 cgaccgcttc gcctccaagc tcccatggaa ggagacccct tccttcggct tccacgaccg   2640
```

-continued

```
cgccgccgcc cccgtcgtcg ccgactactt ctccagcacc ctcggccccg acttcgcgcc      2700 aatgggtaa ttaaaacgat ggtggacgac attgcatttc aaattcaaaa caaattcaaa      2760
acacaccgac cgagattatg ctgaattcaa acgcgtttgt gcgcgcagga gggtgtacca      2820
gaagtactgc gaggagatga aggagctgtc gctgacgatc atggaactcc tggagctgag      2880
cctgggcgtg gagcgaggct actacaggga gttcttcgcg gacagcagct caatcatgcg      2940
gtgcaactac tacccgccat gcccggagcc ggagcggacg ctcggcacgg gcccgcactg      3000
cgaccccacc gccctcacca tcctcctcca ggacgacgtc ggcggcctcg aggtcctcgt      3060
cgacggcgaa tggcgccccg tcagcccgt ccccggcgcc atggtcatca acatcggcga      3120
caccttcatg gtaaaccatc tcctattctc ctctcctctg ttctcctctg cttcgaagca      3180
acagaacaag taattcaagc ttttttttct ctctcgcgcg aaattgacga gaaaataag      3240 atcgtggtag gggcgggget ttcagctgaa agcgggaaga aaccgacctg acgtgatttc      3300
tctgttccaa tcacaaacaa tggaatgccc cactcctcca tgtgttatga tttatctcac      3360
atcttatagt taataggagt aagtaacaag ctacttttt catattatag ttcgtttgat      3420 ttttttttt taaagttttt ttagttttat ccaaatttat tgaaaaactt agcaacgttt      3480
ataataccaa attagtctca tttagtttaa tattgtatat attttgataa tatatttatg      3540
ttatattaaa aatattacta tattttttcta taaacattat taaaagccat ttataatata      3600
aaatggaagg gagtaattaa tatggatctc ccccgacatg agaatatttt ccgatggtgt      3660
gacgacgcca tgtaagcttc ggtgggcctg acggccaga ggtgccaaca gccacgtcca      3720
acaacccctg ggtcccccc taacactcca acagtagtg agtagtgtct cgtcgcgttt      3780
tagtatttga tgacaaacaa agtgtgagtt gagttagcca ccaccaactt gcacacgagc      3840
acatacattt gtgtccattc tcgccagtca cttccatctc tagtcctaac tcctatctag      3900
cgatgtaagc ggataatttc atcatccgta tataaacctg tttgttatag ttaatttcct      3960
atataatact ataacagtat acattttaaa agaaaacaaa attaggataa acaggccctg      4020
ctcctatcca tccatggcac ttggaaggac cagactcggt catgccatgc caagccaaga      4080
tatgggttat ggaagagtag agaagaggag agatgagaga taagcatgcg ttctcctcct      4140
cgttggatgt gtattttgga gggatttgtg tagtagtagc agcggcgccg cggggacgga      4200
tgcggatggt ggcgctttcg gtggcgtttt cccggggggg ttttggtttg gcgcttgggg      4260
gggatggcat ggcgcggcgt gcggctgcac gccacacaca cgcgcgcgca cgcacgtacg      4320
tcgtcgtcgc cgcgggcgga cggtagctta gggtggtgtg ttccgcgcgc gggcgcggat      4380
tgttccatgc cgatcgattt ggcgccaccc tcgccgcggc tcttgtcgcg tcgtgcgcct      4440
ctctcgcgcg gtttgtcctt gtcgcgttgc tcagccggcg acggggcac ggacattggc      4500 gatgtagccc tgcacgtgtc ggcctctccg ttgatgaatg atgatgtatg tatgtatttt      4560
tttttgtctg aaggaatttg tggggaattg ttgtgtgtgc aggcgctgtc gaacgggagg      4620
tataagagct gcctgcacag ggcggtggtg aaccagcggc gggagcggcg gtcgctggcg      4680
ttcttcctgt gcccgcggga ggacagggtg gtgcggccgc cgccgagcgc cgccacgccg      4740
cagcactacc cggacttcac ctgggccgac ctcatgcgct tcacgcagcg ccactaccgc      4800
gccgacaccc gcacgctcga cgccttcacg cgctggctcg cgccgccggc cgccgacgcc      4860
gccgcgacgg cgcaggtcga ggcggccagc tgatcgccga acggaacgaa acggaacgaa      4920
cagaagccga ttttttggcgg ggcccacgcc cacgtgaggc cccacgtgga cagtgggccc      4980
gggcggaggt ggcacccacg tggaccgcgg gccccgcgcc gccttccaat tttggaccct      5040
```

-continued

```
accgctgtac atattcatat attgcaagaa gaagcaaaac gtacgtgtgg gttgggttgg    5100
gcttctctct attactaaaa aaaatataat ggaacgacgg atgaatggat gcttatttat    5160
ttatctaaat tgaattcgaa ttcggctcat ggatttcgcg aatgtggatg gtggatgccc    5220
gcctcgatga atccgctttg tccgatagag aaatttgaat ttaaatccgg gacctggatt    5280
ttgcaatgtg gacgggtgtg ctttgcgaaa tctgctttgt tcgatagcgc tgcacaaaac    5340
atgcggtggg ccctgcatga gaatccgctt cttctttgtt gccttggtag gcgaaatcgt    5400
atatggtccc aacgattttc tttgtttggt ttcaacataa atgggagttt ttatgaattt    5460
aggcttatct acatcagagc tactcctaac ttgtgatatg atgaaccaat cgtgttcttc    5520
tcatacttgt ttaagttggc caatatagga ttaatgcaga gtatccaagg gtttt         5575
```

<210> SEQ ID NO 4
<211> LENGTH: 389
<212> TYPE: PRT
<213> ORGANISM: Oryza sativa

<400> SEQUENCE: 4

```
Met Val Ala Glu His Pro Thr Pro Pro Gln Pro His Gln Pro Pro Pro
  1               5                  10                  15

Met Asp Ser Thr Ala Gly Ser Gly Ile Ala Ala Pro Ala Ala Ala Ala
                 20                  25                  30

Val Cys Asp Leu Arg Met Glu Pro Lys Ile Pro Glu Pro Phe Val Trp
             35                  40                  45

Pro Asn Gly Asp Ala Arg Pro Ala Ser Ala Ala Glu Leu Asp Met Pro
         50                  55                  60

Val Val Asp Val Gly Val Leu Arg Asp Gly Asp Ala Glu Gly Leu Arg
 65                  70                  75                  80

Arg Ala Ala Ala Gln Val Ala Ala Ala Cys Ala Thr His Gly Phe Phe
                 85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
        115                 120                 125

Ala Arg Arg Val Pro Gly Thr Val Ser Gly Tyr Thr Ser Ala His Ala
    130                 135                 140

Asp Arg Phe Ala Ser Lys Leu Pro Trp Lys Glu Thr Leu Ser Phe Gly
145                 150                 155                 160

Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190

Cys Glu Glu Met Lys Glu Leu Ser Leu Thr Ile Met Glu Leu Leu Glu
        195                 200                 205

Leu Ser Leu Gly Val Glu Arg Gly Tyr Tyr Arg Glu Phe Phe Ala Asp
    210                 215                 220

Ser Ser Ser Ile Met Arg Cys Asn Tyr Tyr Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
```

-continued

```
                   275                 280                 285
Gly Asp Thr Phe Met Ala Leu Ser Asn Gly Arg Tyr Lys Ser Cys Leu
    290                 295                 300

His Arg Ala Val Val Asn Gln Arg Arg Glu Arg Arg Ser Leu Ala Phe
305                 310                 315                 320

Phe Leu Cys Pro Arg Glu Asp Arg Val Val Arg Pro Pro Ser Ala
                325                 330                 335

Ala Thr Pro Gln His Tyr Pro Asp Phe Thr Trp Ala Asp Leu Met Arg
                340                 345                 350

Phe Thr Gln Arg His Tyr Arg Ala Asp Thr Arg Thr Leu Asp Ala Phe
                355                 360                 365

Thr Arg Trp Leu Ala Pro Pro Ala Ala Asp Ala Ala Ala Thr Ala Gln
    370                 375                 380

Val Glu Ala Ala Ser
385

<210> SEQ ID NO 5
<211> LENGTH: 9
<212> TYPE: PRT
<213> ORGANISM: Oryza sativa
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 5

Asn Tyr Tyr Pro Xaa Cys Xaa Xaa Pro
1               5

<210> SEQ ID NO 6
<211> LENGTH: 6
<212> TYPE: PRT
<213> ORGANISM: Oryza sativa

<400> SEQUENCE: 6

Leu Pro Trp Lys Glu Thr
1               5
```

GA20 OXIDASE FROM RICE AND USES THEREOF

TECHNICAL FIELD

The present invention relates to the isolation and identification of a gene involved in plant semidwarfing and the semidwarfing of plants utilizing said gene.

BACKGROUND ART

In 1956 in Taiwan, a new rice variety, "Taichung Native 1", gave a high yield that had not been observed with conventional indica varieties. "Taichung Native 1" was bred from a cross between a semidwarf local variety, "Dee-geo-woo-gen", and a disease-resistant gardening variety, "Tsai-yuang-chung". In the late 1960s, a semidwarf variety, "IR8", was similarly bred from a cross between the semidwarf variety "Dee-geo-woo-gen" and an Indonesian high-quality long-culm rice variety, "Peta", at the International Rice Research Institute (IRRI), Philippines. This variety was called "miracle rice", as it dramatically improved the yield per unit area. The spreading of "miracle rice" relieved the food crisis in Asia and gave rise to the "green revolution". The gene that contributed to the high yields of both Taichung Native 1 and IR8 is the semidwarf gene sd1 derived from Dee-geo-woo-gen. However, to date, only the approximate chromosomal locus of the sd1 gene has been determined (Maeda et al., Breeding. Science 47: 317–320, 1997).

In general, plants, particularly useful agricultural crops such as rice, must be cultivated under well-fertilized conditions (i.e., nitrogen-rich conditions) if their yields are to be enhanced. In such conditions however, plants become so tall that they are apt to be blown down by typhoons and such, thereby resulting in the reduction of yields. One method for resolving such problems is to dwarf plants and cultivate them under well-fertilized conditions. The sd1 gene dwarfs plants only slightly and does so without reducing the number of tillers or size of the grain, or decreasing the number of seeds. It also prevents plants from falling down under well-fertilized conditions and improves plant shape. In this manner, the sd1 gene results in phenotypes different from those induced by the already-known dwarf genes, d1 and d61 (Ashikari M. et al., Proc. Natl. Acad. Sci. USA., 96: 10284–10289, 1999; Yamamuro C. et al., Plant Cell, 12: 1591–1605, 2000). This improvement in resistance to falling down enables plant cultivation under fertilized conditions; likewise, the improvement of plant shape enhances substance producing capability and distribution ratio of assimilation products into grains and seeds. To date, utilizing these properties, many rice varieties, including IR64 having the largest rice planted area in the world, have been conferred with phenotypes induced by the sd1 gene through back cross to breed novel rice varieties.

On the other hand, with a recent explosive increase in population, grain yields need to be further increased by 50%, so there is an urgent need to breed varieties of various useful crops with high yields. Therefore, in order to increase the yield of various plants, useful agricultural crops, including rice in particular, it is advantageous to utilize the sd1 gene that induces stable yield increases under fertilized conditions. However, the isolation and identification of the sd1 gene of plants including rice has not yet been reported.

DISCLOSURE OF THE INVENTION

The present invention was made in view of these circumstances. An objective of this invention is to provide the sd1 gene involved in plant semidwarfing. Furthermore, another objective of the present invention is to provide a method for semidwarfing plants using the sd1 gene.

Gibberellin (GA), a plant hormone, is involved in a number of growth processes such as germination, stem/leaf elongation, and formation of flower-buds. The GA synthesis pathway has been studied in detail, and some genes that encode enzymes catalyzing GA synthesis have been isolated from Arabidopsis, rice, maize, pumpkin, and the like. (Hedden and Kamiya, Annu. Rev. Plant Physiol. Plant Mol. Biol. 48: 431–460, 1997). When genes involved in GA synthesis or signal transduction become aberrant, a plant is unable to utilize GA for its growth and, thus, becomes dwarfed. In fact, many reports have shown that deficiencies in genes involved in GA synthesis or signal transduction cause dwarfed mutants (Hedden and Kamiya, Annu. Rev. Plant Physiol. Plant Mol. Biol. 48: 431–460, 1997). Thus, the present inventors postulated that GA was involved in semidwarfing of rice, and administered GA to an sd1 mutant Dee-geo-woo-gen to examine the GA reactivity. As a result, stem/leaf elongation of Dee-geo-woo-gen was caused by GA administration. Furthermore, C20 oxidase, a GA biosynthesis enzyme, catalyzes the following steps: GA53-GA44-GA19-GA20 and GA12-GA15-GA24'-GA9 in the GA biosynthetic pathway. To date, C20 oxidase has been isolated from pumpkin, Arabidopsis, and rice (Lange et al., Proc. Natl. Acad. Sci. USA., 91: 8552–8556, 1994; Phillips et al., Plant physiol. 108: 1049–1057, 1995; Xu et al., Proc. Natl. Acad. Sci. USA., 92: 6640–6644, 1995; Toyomasu et al., Physiol. Plant. 99: 111–118, 1997), and at least three C20 oxidase genes have been reported to be present in the Arabidopsis genome (Phillips et al., Plant Physiol. 108: 1049–1057, 1995).

From the aforementioned knowledge, the present inventors presumed that the sd1 gene is a gene involved in GA biosynthesis, in particular, that it is a C20 oxidase gene repeatedly present in plant genomes. If so, this explains why the rice sd1 gene does not induce a dramatic dwarfing of plant shape. Therefore, the inventors first aimed to isolate and identify the rice counterpart of Arabidopsis C20 oxidase.

As a result, the present inventors succeeded in isolating and identifying a novel rice GA C20 oxidase gene. Furthermore, the inventors examined whether the chromosomal locus of this gene is close to the rice sd1 locus, and also whether the novel rice GA C20 oxidase gene is mutated in rice semidwarf varieties. In consequence, it was discovered that the chromosomal locus of the gene is extremely close to that of the rice sd1. In addition, when the nucleotide sequences of the GA C20 oxidase genes in several sd1 mutants comprising Dee-geo-woo-gen and corresponding wild types were determined and compared, such GA C20 oxidase genes were mutated in all sd1 mutants examined. Therefore, it was revealed for the first time that the rice sd1 gene is identical to a gene encoding a novel C20 oxidase, indicating that mutation of the plant sd1 gene (C20 oxidase gene) would induce semidwarfing of plants.

The plant sd1 gene can be used in the efficient breeding by marker selection. When a variety introduced with the sd1 gene is prepared using the conventional cross breeding, for example, when Koshihikari, which is the most widely cultivated rice variety in Japan, is introduced with the sd1 gene, it is necessary to prepare F1s by crossing Koshihikari with IR64 or such having the sd1 gene, followed by backcrossing the F1s with Koshihikari repeatedly until all the chromosomes other than the sd1 gene locus are substituted with those of Koshihikari. Isolation of the sd1 gene permits the saving of a great deal of time and labor required for breeding since the use of the sd1 gene as a molecular marker allows one to efficiently select individual plants having Koshihikari chromosomes substituted only with the sd1 gene. Furthermore, the use of the plant sd1 gene permits the production of plant transformants using molecular biological techniques, such as antisense and RNAi methods. It is also expected to enhance the yield of useful agricultural crops, including grains such as wheat, barley, and maize, vegetables, and fruit plants, and furthermore, provide aesthetic values to ornamental plant-s, such as foliage plants, through dwarfing, resulting in the production of novel varieties.

Specifically, the present invention relates to the isolation and identification of a gene involved in plant semidwarfing, and semidwarfing of plants using the sd1 gene, more specifically provides the following:

[1] a DNA according to any one of (a) to (c) for semidwarfing a plant:

(a) a DNA encoding an antisense RNA complementary to a transcriptional product of a plant sd1 gene;

(b) a DNA encoding an RNA having a ribozyme activity to specifically cleave the transcriptional product of the plant sd1 gene; and (c) a DNA encoding an RNA inhibiting expression of the plant sd1 gene through co-suppression effects;

[2] the DNA of [1], wherein said plant sd1 gene is the rice sd1 gene;

[3] a vector comprising the DNA of [1] or [2];

[4] a transformed plant cell retaining the DNA of [1] or [2] in an expressible state;

[5] the transformed plant cell of [4], wherein said plant is rice;

[6] a plant transformant comprising the transformed plant cell of [4] or [5];

[7] a plant transformant that is a descendant or clone of the plant transformant of [6];

[8] the plant transformant of [6] or [7], wherein said plant is rice;

[9] a breeding material of the plant transformant of any one of [6] to [8];

[10] a method for producing the plant transformant of any one of [6] to [8], wherein said method comprises the steps of: introducing the DNA of [1] or [2] into a plant cell, and regenerating a plant body from said plant cell;

[11] a method for semidwarfing a plant, wherein said method comprises the step of suppressing the expression of the endogenous sd1 gene in plant cells;

[12] the method of [11], wherein suppression of expression is achieved by introducing the DNA of [1] or [2] into a plant;

[13] the method of any one of [10] to [12], wherein said plant is rice; and

[14] a DNA encoding the rice sd1 protein.

The present invention revealed that mutation of the plant sd1 gene induces plant semidwarfing. Therefore, it is possible to produce a semidwarf variety giving stable high yields under fertilized conditions by suppressing expression of the plant sd1 gene.

In the context of the present invention, the term "plant semidwarfing" merely refers to a slight dwarfing of plant height without reducing the number of tillers, the size of grains, or number of seeds. By this semidwarfing, the plant is conferred a resistance to falling-down under fertilized conditions and its shape is improved. As a result, a stable high yield can be obtained.

In the context of the present invention, the expression "plant sd1 gene" refers to a gene encoding a plant C20 oxidase, and includes the rice sd1 gene (DNA encoding SEQ ID NOs: 3 and 4), *Arabidopsis* sd1 gene (Phillips et al., Plant physiol. 108: 1049–1057, 1995), and sd1 genes derived from other plants.

Identification of an unknown "plant sd1 gene" can be performed using hybridization (Southern et al., Journal of Molecular Biology 98: 503, 1975) and polymerase chain reaction (PCR) (Saiki et al., Science 230: 1350–1354, 1985; Saiki et al., Science 239: 487–491, 1988) techniques. That is, one skilled in the art can isolate DNAs highly homologous to the sd1 gene from other desired plants and determine their sequences, for example, by using as a probe the nucleotide sequence of rice sd1 gene (DNA encoding SEQ ID NOs: 3 and 4), or a portion of it, or by using as a primer oligonucleotides specifically hybridizing to the sd1 gene nucleotide sequence.

Hybridization reactions are usually conducted under stringent conditions to isolate such DNAs. Stringent hybridization conditions include conditions such as: 6 M urea, 0.4% SDS, and 0.5× SSC; and those with a similar stringency to that condition. Isolation of DNAs with higher homology may be achieved by performing hybridization under conditions of higher stringency, for example, 6 M urea, 0.4% SDS, and 0.1×SSC. Isolated DNAs can be sequenced by known methods.

Whether the isolated DNA is a DNA encoding an sd1 protein is commonly judged from the degree of homology between sequences. Sequence homology can be determined using programs such as BLASTN (nucleic acid sequence level) and BLASTX (amino acid sequence level) (Altschul et al. J. Mol. Biol. 215: 403–410, 1990). Such programs are based on the algorithm "BLAST" described by Karlin and Altschul (Proc. Natl. Acad. Sci. USA 87: 2264–2268, 1990; Proc. Natl. Acad. Sci. USA 90: 5873–5877, 1993). When nucleotide sequences are analyzed according to BLASTN, parameters are set, for example, as score=100 and word length=12. On the other hand, to analyze amino acid sequences by BLASTX, parameters are set, for example, as score=50 and word length=3. Furthermore, when amino acid sequences are analyzed using Gapped BLAST program, analysis can be performed as described by Altschul et al. (Nucleic Acids Res. 25: 3389–3402, 1997). Default parameters of each program are used when BLAST and Gapped BLAST program are used. Specific techniques for such analyses are known in the art (available on the web site of the National Center for Biotechnology Information (NCBI), National Library of Medicine, Building 38A, Bethesda, Md. 20894, U.S.A.).

In this invention, there is no particular limitation on the types of plants to be conferred with a semidwarf property by suppressing the sd1 gene expression. Thus, any plants can be semidwarfed, though it is preferable to utilize useful agricultural crops and ornamental plants. Useful agricultural crops include, for example, monocotyledonous plants, such as rice, maize, wheat, and barley, and dicotyledonous plants, such as rapeseed, soybean, cotton, tomato, and potato. Ornamental plants include ornamental flowers, such as chrysanthemum, rose, carnation, and cyclamen.

A plant transformant semidwarfed according to the present invention is created by inserting a DNA that suppresses the expression of the sd1 gene into an appropriate vector, introducing this vector into a plant cell, and then regenerating the resulting transformed plant cell. The phrase "suppression of the sd1 gene expression" refers to suppression of sd1 gene transcription as well as suppression of translation to protein. It also encompasses not only the complete cessation of DNA expression but also a reduction in such expression.

The expression of a specific endogenous gene in plants can be suppressed using antisense technology methods which are commonly used in the art. Ecker et al. were the first to demonstrate the antisense effect of an antisense RNA introduced by electroporation into plant cells using the transient gene expression method (Ecker and Davis (1986) Proc. Natl. Acad. Sci. USA 83: 5372). Thereafter, the target gene expression was reportedly reduced in tobacco and petunias by expressing antisense RNAs (Krol et al. (1988) Nature 333: 866). The antisense technique has now been established as a means to suppress target gene expression in plants. Multiple factors cause suppression of target gene expression by an antisense nucleic acid. These include: inhibition of transcription initiation resulting from triple strand formation; suppression of transcription resulting from hybrids formed at the site where the RNA polymerase has formed a local open loop structure; transcription inhibition resulting from hybrid formation with the RNA being synthesized; suppression of splicing resulting from hybrid formation at the junction between an intron and an exon; suppression of splicing resulting from hybrid formation at the site of spliceosome formation; suppression of mRNA translocation from the nucleus to the cytoplasm resulting from hybrid formation with mRNA; suppression of splicing resulting from hybrid formation at the capping site or at the poly A addition site; suppression of translation initiation resulting from hybrid formation at the binding site for the translation initiation factors; suppression of translation resulting from hybrid formation at the site for ribosome binding near the initiation codon; inhibition of peptide chain elongation resulting from hybrid formation in the translated region or at the polysome binding sites of mRNA; and suppression of gene expression resulting from hybrid formation at the sites of interaction between nucleic acids and proteins. These factors suppress the target gene expression by inhibiting the process of transcription, splicing, and/or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)", Nihon Seikagakukai (The Japanese Biochemical Society) (ed.), Tokyo Kagaku Dozin, pp. 319–347, (1993)).

Accordingly, an antisense sequence of the present invention can suppress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention includes DNA having antisense sequences against both the untranslated regions and the translated regions of the gene. The antisense DNA to be used is connected downstream of an appropriate promoter, and, preferably, a sequence containing the transcription termination signal is connected on the 3' side.

Antisense DNA can be prepared based on the sequence information of the DNA according to SEQ ID NO: 3, for example, by the phosphorothioate method (Stein, Nucleic. Acid. Res. 16: 3209–3221, 1988). The prepared DNA can be transfected into the desired plant by known methods. The sequence of the antisense DNA is preferably a sequence complementary to the endogenous gene of the plant to be transformed or a part thereof, but it need not be perfectly (100%) complementary, so long as it can effectively inhibit the gene expression. The transcribed RNA is preferably 90% or more, and even more preferably 95% or more complementary to the transcribed products of the target gene. In order to effectively inhibit the expression of the target gene by means of an antisense sequence, the antisense DNA should be at least 15 nucleotides or more in length, preferably 100 nucleotides or more, and more preferably 500 nucleotides or more. The antisense DNA to be used is generally shorter than 5 kb, and preferably shorter than 2.5 kb.

DNAs encoding ribozymes can be used to suppress the expression of an endogenous gene. A ribozyme is an RNA molecule that has catalytic activities. There are many ribozymes having various activities. Research on ribozymes as RNA cleaving enzymes has enabled the design of a ribozyme that site-specifically cleaves RNA. While ribozymes such as those of the group I intron-type and MIRNA contained in RnaseP can be large, with 400 nucleotides or more, there are smaller ones as well, including the hammerhead type and the hairpin type that have an activity domain of about 40 nucleotides or more (Koizumi and Ohtsuka (1990) Tanpakushitsu Kakusan Kohso (Protein, Nucleic acid, and Enzyme) 35: 2191).

The self-cleavage domain of a hammerhead type ribozyme cleaves at the 3' side of C15 of the sequence G13U14C15. Formation of a nucleotide pair between U14 and A at the ninth position is considered to be important for the ribozyme activity. Furthermore, it has been shown that the cleavage also occurs when the nucleotide at the 15th position is A or U instead of C (Koizumi et al. (1988) FEBS Lett. 228: 225). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (Koizumi et al. (1988) FEBS Lett. 239: 285; Koizumi and Ohtsuka (1990) Tanpakushitsu Kakusan Kohso (Protein, Nucleic acid, and Enzyme), 35: 2191; Koizumi et al. (1989) Nucleic Acids Res. 17: 7059).

The hairpin type ribozyme is also useful in the present invention. A hairpin type ribozyme can be found, for example, in the minus strand of the satellite RNA of tobacco ringspot virus (Buzayan (1986) Nature 323: 349). This ribozyme has also been shown to target-specifically cleave RNA (Kikuchi and Sasaki (1992) Nucleic Acids Res. 19: 6751; Kikuchi (1992) Kagaku To Seibutsu (Chemistry and Biology) 30: 112).

A ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (Taira et al. (1990) Protein Eng. 3: 733; Dzaianott and Bujarski (1989) Proc. Natl. Acad. Sci. USA 86: 4823; Grosshands and Cech (1991) Nucleic. Acids. Res. 19: 3875; Taira et al. (1991) Nucleic. Acid. Res. 19: 5125). Multiple sites within a target gene can be cleaved by arranging these structural units in tandem to achieve greater effects (Yuyama et al., Biochem. Biophys. Res. Commun. 186: 1271 (1992)). Using such ribozymes, it is possible to specifically cleave the transcription products of a target gene of the present invention, thereby suppressing the expression of the gene.

Endogenous gene expression can also be suppressed by co-suppression, through transformation with a DNA having a sequence identical or similar to the target gene sequence. "Co-suppression" refers to the phenomenon wherein, when a gene having a sequence identical or similar to the target endogenous gene sequence is introduced into plants by transformation, expression of both the introduced exogenous gene and the target endogenous gene becomes suppressed. Although the detailed mechanism of co-suppression is not fully understood, it is frequently observed in plants (Curr. Biol. 7: R793, 1997; Curr. Biol. 6: 810, 1996). For example, if one wishes to obtain a plant body in which the sd1 gene is co-suppressed, the plant in question can be transformed with a vector DNA designed to express the sd1 gene or DNA having a similar sequence to select a plant having a property of the sd1 mutant, i.e. a semidwarfed plant, among the resultant plants. The gene to be used for co-suppression need not be completely identical to the target gene, but it should have at least 70% or more, preferably 80% or more, and more preferably 90% or more (e.g. 95% or more) sequence identity thereto.

In addition, endogenous gene expression in the present invention can also be suppressed by transforming the plant with a gene having the dominant negative phenotype of the target gene. A gene having the dominant negative phenotype refers to a gene which, when expressed, can eliminate or reduce the activity of the wild type endogenous gene inherent to the plant.

The present invention also provides vectors comprising DNAs capable of suppressing the expression of an above-described endogenous gene, transformed plant cells retaining such DNAs in an expressible state, plant transformants comprising the transformed plant cells, plant transformants that are progenies or clones of the above plant transformants, and breeding material from the plant transformants.

Furthermore, this invention relates to a method for producing an aforementioned plant transformant, comprising the steps of: introducing a DNA capable of suppressing the expression of an endogenous gene into plant cells; and regenerating a plant from the plant cells.

DNAs of this invention can be introduced into plant cells by methods known to one skilled in the art, such as the *Agrobacterium*-mediated transfer method, the electroporation method, and the particle bombardment method.

As the above-described *Agrobacterium* method, for example, the method of Nagel et al. (Microbiol. Lett. 67: 325, 1990) may be used. According to this method, a recombinant vector is transformed into *Agrobacterium* bacterial cells, and then the transformed *Agrobacterium* is introduced into plant cells by known methods, such as the leaf disk method. The above-described vector, for example, comprises a promoter that allows the DNA of this invention to be expressed after its introduction into a plant. In general, the DNA of this invention is localized downstream of such a promoter, and furthermore a terminator lies downstream of the DNA. Recombinant vectors used for such a transformation are appropriately selected by one skilled in the art, depending on the transformation method or the type of a plant. The aforementioned promoters include, for example, the CaMV35S promoter derived from cauliflower mosaic virus and ubiquitin promoter of maize (Unexamined Published Japanese Patent Application No. (JP-A) Hei2–79983).

Furthermore, the above-described terminators include one derived from the cauliflower mosaic virus and one derived from the nopaline synthase gene. However, the invention is not limited thereto; any promoters or terminators that can function in plants may be used.

In addition, the plant into which a DNA of this invention is introduced may be an explanted graft. Alternatively, cultured cells may be prepared from these plants, and such DNA may be introduced into the cultured cells. In the context of the present invention, the term "plant cells" includes, for example, cells from leaves, roots, stems, flowers, seed scutellum, calluses, and culture cell suspensions.

Furthermore, for efficiently selecting plant cells transformed by introduction of a DNA of this invention, the above-described recombinant vectors preferably contain an appropriate selection marker gene, or are preferably introduced into plant cells together with a plasmid vector comprising such a selection marker gene. Selection marker genes used herein include, for example, the hygromycin phosphotransferase gene resistant to the antibiotic hygromycin, the neomycin phosphotransferase gene resistant to kanamycin or gentamycin, and the acetyltransferase gene resistant to a herbicide, phosphinothricin.

Plant cells introduced with recombinant vectors are plated and cultured on known selection media comprising an appropriate selection drug, which varies according to the type of introduced selection marker gene. As a result, transformed plant cultured cells can be obtained.

Plants can then be regenerated from the plant cells transformed with the DNA according to the present invention. Plant regeneration can be performed by known methods depending on the type of the plant cell (Toki et al., (1995) Plant Physiol. 100:1503–1507). For example, transformation and regeneration methods for rice plants include: (1) introducing genes into protoplasts using polyethylene glycol, and regenerating the plant body (suitable for indica rice varieties) (Datta et al., (1995) in "Gene Transfer To Plants", Potrykus I— and Spangenberg Eds., pp 66–74); (2) introducing genes into protoplasts using electric pulse, and regenerating the plant body (suitable for japonica rice varieties)(Toki et al. (1992) Plant Physiol. 100: 1503–1507); (3) introducing genes directly into cells through particle bombardment, and regenerating the plant body (Christou et al. (1991) Bio/Technology, 9: 957–962); and (4) introducing genes using *Agrobacterium*, and regenerating the plant body (Hiei et al. (1994) Plant J. 6: 271–282). These methods are already established and widely used in the art. Accordingly, such methods can be suitably used in the present invention.

A plant body regenerated from transformed cells is then cultured in a conditioned medium. When the acclimatized regenerated plant body is subsequently cultivated under the usual culture condition, a semidwarf plant body is obtained, which then matures and fruits to yield seeds.

Herein, the presence of the introduced foreign DNA can be confirmed in the plant transformant which has been regenerated and cultivated as mentioned above, by the known PCR or Southern hybridization methods, or through nucleotide sequence analysis of the DNA in the plant body.

In this case, DNA extraction from the plant transformant can be conducted according to the known method of J. Sambrook et al. (Molecular Cloning, $2^{nd}$ ed, Cold Spring Harbor Laboratory Press, 1989).

When a foreign gene comprising a DNA of this invention present in the regenerated plant body is analyzed using PCR method, amplification reaction is performed using as a template the DNA extracted from the regenerated plant body as described above. Furthermore, synthetic oligonucleotides having nucleotide sequences appropriately selected according to those of the DNA of this invention or the DNA modified by this invention can be used as primers to perform amplification reaction in a reaction solution comprising the mixture of such oligonucleotides. In the amplification reaction, amplified products of DNA fragments comprising a DNA sequence of this invention can be obtained by repeating the denaturation, annealing, and elongation reactions of DNA several ten times. When a reaction solution comprising amplification products is, for example, electrophoresed on agarose gel, various amplified DNA fragments are fractionated to confirm how that DNA fragment corresponds to the DNA of this invention.

Once a transformed plant, in which a DNA of the present invention is introduced into the chromosome, is obtained, it is possible to gain descendants from that plant body by sexual or vegetative propagation. Alternatively, plants can be mass-produced from breeding materials (for example, seeds, fruits, ears, tubers, tubercles, tubs, callus, and protoplast) obtained from the original transformed plant, as well as its descendants or clones. Plant cells transformed with a DNA of the present invention, plant bodies including these cells, descendants and clones of the plant, as well as breeding materials obtained from the plant, its descendant, and clones, are all comprised in the present invention.

In the present invention, plant semidwarfing can be induced by suppressing the expression of the sd1 gene as described above. Semidwarfed plants produced by the method of this invention are expected to, for example, be useful as agricultural crops that can stably give high yields, and also provide novel aesthetic values to ornamental plants.

Furthermore, this invention provides a DNA encoding the rice sd1 protein. The sd1 DNA may be used in the plant growth promotion, especially in enhancement of the stem/leaf elongation. Preparation of a plant transformant using a DNA encoding the rice sd1 protein can be performed by the above-described method. Namely, such preparation can be carried out by inserting the DNA into the aforementioned vector, introducing the resulting recombinant vector into plant cells, and regenerating a plant body from the transformed plant cells. Furthermore, based on the DNA sequence encoding the rice sd1 protein of this invention, it is possible to prepare DNA encoding antisense RNA, DNA encoding RNA having the ribozyme activity and further DNA encoding RNA having co-suppression effects and so on, which are used to suppress the expression of the plant sd1 gene. DNAs thus prepared can be used to induce plant semidwarfing.

The "rice sd1 protein" in the present invention comprises not only a protein of SEQ ID NO: 4 but also rice-derived proteins functionally equivalent to that protein. Such proteins include both those which are artificially prepared and those endogenously present in rice. Herein, the term "functionally equivalent" indicates that the protein of interest has the GA synthesis activity and stem/leaf elongation activity when introduced into plants. Such proteins include mutants, homologues, and variants of the protein according to SEQ ID NO: 4.

Proteins functionally equivalent to the rice sd1 protein can be prepared using, for example, a mutagenesis method known to one skilled in the art for introducing mutation(s) in the amino acid sequence of a protein [e.g. site-directed mutagenesis method (Ausubel et al., Current Protocols in Molecular Biology edit. Publish. Johon Wily & Sons Section 8: 1–8.5, 1987)]. Furthermore, endogenous proteins in rice produced by amino acid mutation(s) arising nature can be isolated based on DNA of SEQ ID NO: 3, using hybridization techniques, gene amplification techniques (PCR), and the like.

Proteins having the amino acid sequence of SEQ ID NO: 4 in which one or more amino acids are substituted, deleted, inserted, and/or added, are included in this invention so long as they have a function equivalent to that of the rice sd1 protein. The number of mutations in the protein is typically 30 amino acids or less, preferably 10 amino acids or less, more preferably 5 amino acids or less (for example, 3 amino acids or less); however, there is no limitation in the number and site of mutations so long as the protein function is retained. From the aspect of retaining the protein function, an amino acid for substitution preferably has a similar property to that of amino acid being substituted. For example, since Ala, Val, Leu, Ile, Pro, Met, Phe, and Trp are all classified into non-polar amino acids, they are likely to have similar properties each other. Furthermore, non-charged amino acids include Gly, Ser, Thr, Cys, Tyr, Asn, and Gln. In addition, acidic amino acids are exemplified by Asp and Glu, while basic amino acids by Lys, Arg, and His.

In this invention, there is no particular limitation on the type of DNAs encoding a rice sd1 protein, so long as they are capable of encoding the above-described protein; they may be genomic DNAs, chemically synthesized DNAs or cDNA. In addition, DNAs of this invention comprise those having arbitrary nucleotide sequences based on degeneracy of genetic codes, so long as they are capable of encoding a rice sd1 protein. DNAs encoding a rice sd1 protein of this invention can be isolated as described above, by standard methods such as hybridization techniques using the DNA sequence of SEQ ID NO: 3 or its portion as probes and gene amplification methods (PCR) using primers designed based on information on such DNA sequences. These probes and primers can be easily prepared by one skilled in the art using known techniques, based on the DNA encoding the rice sd1 protein of this invention.

BEST MODE FOR CARRYING OUT THE INVENTION

Figure 1:
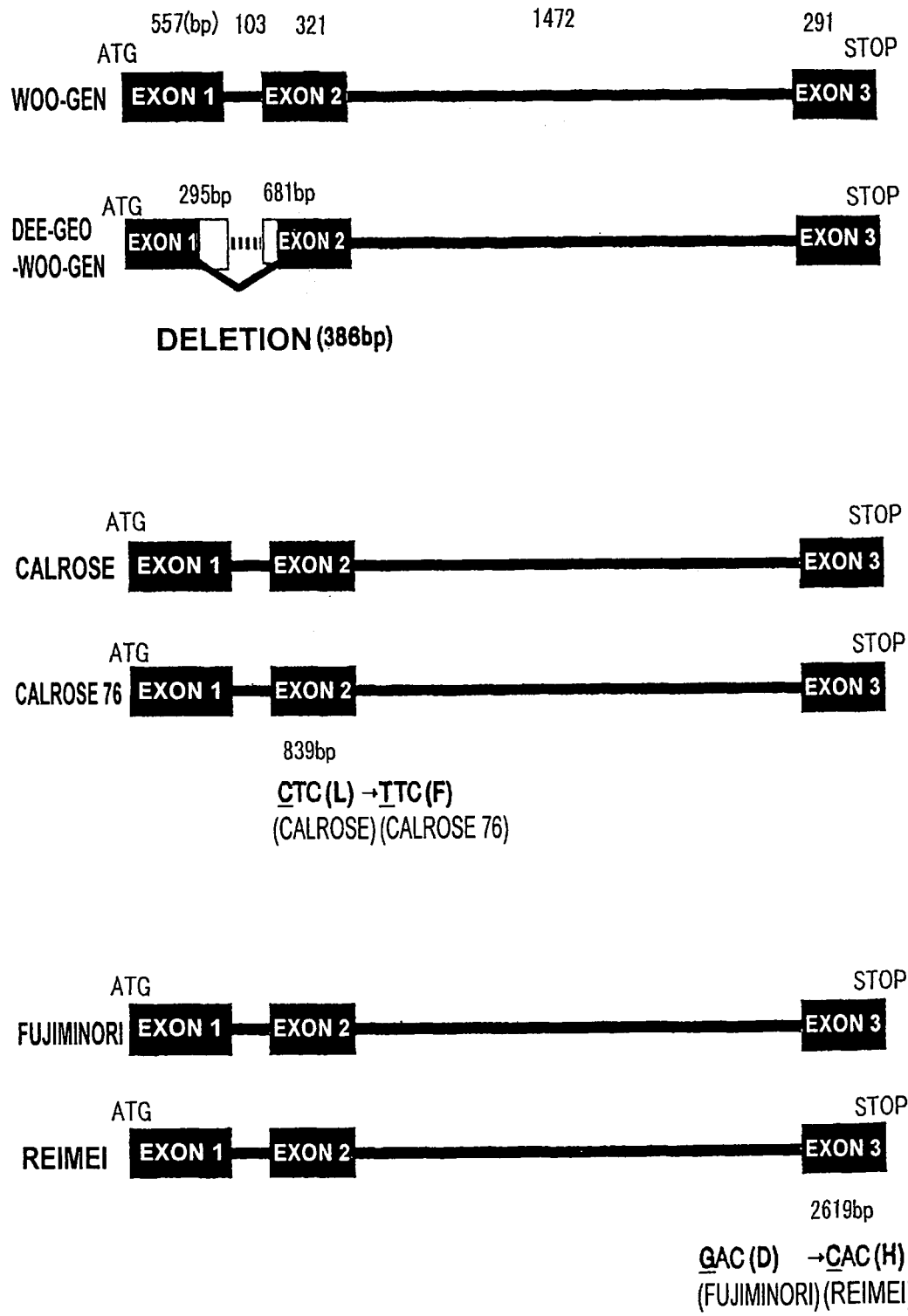
FIG. 1 is a diagram showing mutation sites of the sd1 gene in Dee-geo-woo-gen, Calrose 76, and Reimei.

Herein below, the present invention is more specifically described using Examples. However, the present invention should not to be construed as being limited thereto.

EXAMPLE 1

Based on the sequence of the *Arabidopsis* C20 oxidase gene, primers OsC20U (5'-ccgctcgccgagaagcgccg-3'/SEQ ID NO: 1) and OsC20L (5'-atgaaggtgtcgccgatgtt-3'/SEQ ID NO: 2) were designed. PCR was performed with the Nipponbare rice genomic DNA as a template, aiming to isolate the GA C20 oxidase gene of rice. As a result, an amplification product of 618 bp was obtained, and sequenced to reveal that it is a novel GA oxidase gene of rice. GAC20 belongs to the 2-oxoglutarate-dependent dioxygenase (2-ODD) family, conserving the functionally essential domain (NYYPXCXXP/SEQ ID NO: 5) for binding to 2-oxoglutarate. Furthermore, GAC20 also conserves three histidine residues to bind the Fe ion and the LPWKET (SEQ ID NO: 6) domain that may be involved in GA binding. The rice GAC20 gene shows a 50% homology to that of *Arabidopsis*. [Example 2].

EXAMPLE 2

Linkage analysis for the chromosomal locus of this novel GAC20 oxidase gene using BIL (1998; TAG 96: 997–1003, Mapping quantitative trait loci controlling seed dormancy and heading date in rice, Oryza sativa L., using backcross inbred lines.) revealed that the gene is located at about 155 cM on Rice Chromosome 1. This locus is extremely close to the locus of the sd1 gene, a fact which strongly indicates a possibility that the rice C20 oxidase gene is identical to the sd1 gene.

EXAMPLE 3

A genomic library was constructed from the wild type Nipponbare, and genome clones comprising the GAC20 oxidase gene were isolated using plaque hybridization methods to determine the whole nucleotide sequence of the gene (SEQ ID NO: 3). The deduced amino acid sequence of GAC20 oxidase is set forth in SEQ ID NO: 4.

EXAMPLE 4

Nucleotide sequences of GAC20 oxidase gene in the sd1 mutant Dee-geo-woo-gen and the corresponding wild type Woo-gen were determined for comparison. It was thus discovered that a nucleotide sequence of 386 bp extending from exon 1 to exon 2 was deleted in Dee-geo-woo-gen. Nucleotide sequences of GAC20 oxidase gene in other sd1 mutants were also determined. As a result, in an sd1 mutant Calrose 76, one nucleotide (cytosine) in exon 2 was replaced by thymine, and on the amino acid level, leucine was substituted with phenylalanine. Similarly in an sd1 mutant Reimei, one nucleotide (guanine) in exon 3 was changed to cytosine, and on the amino acid level, aspartic acid was substituted with histidine (FIG. 1).

INDUSTRIAL APPLICABILITY

The present invention provides a plant sd1 gene and a method for utilizing the gene to semidwarf plants. It is highly expected that utilization of plant sd1 genes would enable the enhancement of the yield of plants, particularly useful agricultural crops and ornamental plants, add aesthetic value to ornamental plants through dwarfing, and furthermore, increase the yield and efficient breeding of dwarfed plants by marker selection.

---

The invention claimed is:

1. An isolated cDNA encoding a rice sd1 protein comprising the amino acid sequence of SEQ ID NO:4.

2. A vector comprising the cDNA of claim 1 operably linked to a promoter that functions in rice plant cells.

3. A transformed rice plant cell comprising the vector of claim 2.

4. A transformed rice plant comprising the transformed rice plant cell of claim 3.

5. A transformed rice plant, wherein said plant is a descendent or a clone of the transformed rice plant of claim 4, and wherein said plant comprises the vector.

6. A breeding material of the transformed rice plant of claim 4 or 5.

7. A method for producing a transformed rice plant, wherein said method comprises the steps of:
   (i) introducing the vector of claim 2 into a rice plant cell to obtain a transformed rice plant cell; and
   (ii) regenerating a rice plant from said transformed rice plant cell.

8. A method for promoting growth of a rice plant, wherein said method comprises the steps of
   (i) introducing the vector of claim 2 into a rice plant cell to obtain a transformed rice plant cell; and
   (ii) regenerating a rice plant from said transformed rice plant cell.

* * * * *

UNITED STATES PATENT AND TRADEMARK OFFICE
CERTIFICATE OF CORRECTION

| | |
|---|---|
| PATENT NO. | : 7,138,567 B2 |
| APPLICATION NO. | : 10/481381 |
| DATED | : November 21, 2006 |
| INVENTOR(S) | : Miho Okawa et al. |

Page 1 of 1

It is certified that error appears in the above-identified patent and that said Letters Patent is hereby corrected as shown below:

In Claim 5, column 19, line 64, replace "descendent" with --descendant--

In Claim 8, column 20, line 61, replace "steps of" with --steps of:--

Signed and Sealed this

Ninth Day of October, 2007

JON W. DUDAS
*Director of the United States Patent and Trademark Office*